United States Patent
Van Den Heuvel et al.

(10) Patent No.: US 11,612,568 B2
(45) Date of Patent: Mar. 28, 2023

(54) MINI-TABLETS

(71) Applicant: DFE Pharma GmbH & Co. KG, Goch (DE)

(72) Inventors: Korinde Van Den Heuvel, Wageningen (NL); Bas Van Laarhoven, Wageningen (NL); Eva Maria Janssen, Wageningen (NL); Mara Maria Wilhelmina Van Haandel, Wageningen (NL)

(73) Assignee: DFE PHARMA GMBH & CO. KG, Goch (DE)

( * ) Notice: Subject to any disclaimer, the term of this patent is extended or adjusted under 35 U.S.C. 154(b) by 18 days.

(21) Appl. No.: 16/852,342

(22) Filed: Apr. 17, 2020

(65) Prior Publication Data
US 2020/0237672 A1    Jul. 30, 2020

Related U.S. Application Data

(63) Continuation of application No. PCT/EP2018/078315, filed on Oct. 17, 2018.

(30) Foreign Application Priority Data

Oct. 18, 2017  (EP) ..................... 17197153

(51) Int. Cl.
 *A61K 9/20* (2006.01)
 *A61K 31/167* (2006.01)

(52) U.S. Cl.
 CPC .......... *A61K 9/2018* (2013.01); *A61K 31/167* (2013.01)

(58) Field of Classification Search
 CPC .................. A61K 9/2018; A61K 31/167
 See application file for complete search history.

(56) References Cited

U.S. PATENT DOCUMENTS 8,173,173 B2 * 5/2012 Kussendrager .......... C13K 5/00
                                                          424/499
2013/0224293 A1   8/2013 Dokou et al.

FOREIGN PATENT DOCUMENTS

| EP | 2 229 156 A1 | 9/2010 |
| JP | 2008-525431 | 7/2008 |
| JP | 2014-156435 | 8/2014 |
| WO | WO-2006/068484 A2 | 6/2006 |

OTHER PUBLICATIONS

International Search Report received in corresponding International Application No. PCT/EP2018/078315, 3 pages.
Lennartz, P., et al., "Minitabletting: improving the compactability of paracetamol powder mixtures", International Journal of Pharmaceutics, vol. 173,(1998), pp. 75-85, XP55465276.
P. Lennartz et al.:"Minitabletting: improving the compactability of paracetamol powder mixtures", International Journal of Pharmaceutics, vol. 173, No. 1-2, Oct. 1, 1998 (Oct. 1, 1998), pp. 75-85.

* cited by examiner

*Primary Examiner* — Snigdha Maewall
(74) *Attorney, Agent, or Firm* — Sunit Talapatra; Foley & Lardner LLP

(57) ABSTRACT

The invention relates to a method for making a tablet having a diameter, as determined by the longest enveloping circle, in the range of 1 to 5 mm and/or a weight in the range of 1 to 100 mg—comprising an active ingredient selected from the group of pharmaceutical substances and active substances for a dietary supplement or nutraceutical, comprising
 (a) providing a lactose agglomerate comprising lactose, and a sugar alcohol;
 (b) providing the active ingredient;
 (c) mixing the agglomerate and the active ingredient, thereby obtaining a mixture; and
 (d) forming the tablet by direct compression.

19 Claims, No Drawings

MINI-TABLETS

CROSS-REFERENCE TO RELATED APPLICATIONS

This application is a continuation of International Application No. PCT/EP2018/078315, filed Oct. 17, 2018, which claims the benefit of and priority to European Application No. 17197153.4 filed Oct. 18, 2017, both of which are hereby incorporated by reference herein in their entireties.

TECHNICAL FIELD OF THE INVENTION

The present invention relates to the fields of manufacturing of pharmaceuticals, nutraceuticals or food supplements. In particular, the invention relates to a method for making a tablet, comprising a pharmaceutical substance or an active substance for a dietary supplement. The invention further relates to a tablet comprising such substance, to a method for making an agglomerate respectively and to an agglomerate suitable for use in making the tablet.

BACKGROUND OF THE INVENTION

Pharmaceuticals, nutraceuticals or dietary supplements in the form of small unit dosage form-, in particular mini-tablets, allow the administration of pharmaceuticals, nutraceuticals or dietary supplements with improved comfort; they are more easily swallowed than such products in a larger unit-dosage form. This is also beneficial for realizing an increased patient- or consumer-compliance. Besides, for unit dosage forms that are intended to disintegrate in the mouth or that are intended to be dissolved there is a benefit, as the smaller size may allow a faster disintegration of the dosage form.

Solid pharmaceuticals, nutraceuticals and dietary supplements, in particular tablets and the like, typically comprise one or more active ingredients, one or more excipients e.g. lubricants, disintegrants, fillers, carriers, and optionally one or more further ingredients, e.g. flavours, colourants etc. Pharmaceutical, nutraceutical and dietary supplement active ingredients generally have relatively poor 'compressibility' (the ability of a powder to decrease in volume under pressure), and/or a poor 'compactibility' (the ability of the powdered material to be compressed into a tablet of specified strength). Thus, there is generally a need for improved tabletability of such actives. The active ingredient is therefore usually mixed with a filler excipient to improve tableting.

The production of small-size unit dosage forms (generally having a diameter of 5 mm or less, and typically having a diameter of about 1 to about 3 mm), such as mini-tablets, is particularly challenging. In order to be able to provide the same dose of active ingredient(s) in a single unit dosage form, a relatively higher active-ingredient-load is obtained. Accordingly, the maximum content of excipient is reduced. Improved compaction behaviour of the excipient is important for satisfactory forming of the unit dosage form. Also, good free-flowing properties are particularly important. This is amongst other relevant in a method wherein use is made of a die or mould, in order to achieve effective and efficient filling of the inherently small die or mould cavities wherein the unit dosage forms are formed. In mass production this is particular important to obtain a plurality of unit dosage forms of essentially the same size and weight. Further, improved flow properties of the excipient are needed in order to obtain a small unit dosage form with satisfactory weight uniformity. Moreover, a problem encountered with the production of mini-unit dosage forms, especially when using a direct compression technique is "capping"; especially at a relatively high production speed (such as tabletting speed), capping or lamination is a commonly known problem in the art of producing pharmaceutical, nutraceutical and dietary supplement tablets and the like. In the production of mini-tablets and the like, a high rejection percentage of products due to capping or lamination is in particular problematic.

WO 2011/025673 is specifically directed to multi-layered mini-tablets for oral administration of a pharmaceutical ingredient. It comprises a core mini-tablet, formed by an immediate release layer and a modified release layer, and a coating. It refers in general terms to the preparation of the release layers, e.g. by direct compression with an excipient, such as carbohydrates (sugars, polysaccharides) or protein fillers or inorganics. Problems typically encountered with the manufacture of mini-tablets are not specifically addressed, let alone is the importance of the excipient of choice acknowledged.

Various excipients are known in the art, but to the best of the inventors knowledge none specifically address all the needs for an excipient for the production of small-sized unit dosage forms, such as mini-tablets. The publications and products discussed next relate to tableting excipients but do not specifically disclose the production of mini-unit dosage forms.

EP 509 606 A1 relates to a (non-agglomerated) tableting excipient for making tablets by direct tableting in the form of a homogeneous mass of a roller-dried solution of lactose having a high beta-lactose content to which solution 1-15 wt. % of a sugar alcohol (based on solids of the solution to be dried) has been added prior to drying. This excipient is stated to provide a higher hardness than an excipient without the sugar alcohol. For a high drug load with a poorly tabletable ingredient, such as paracetamol, the inclusion of cellulose is recommended. In Example 4, tablets comprising a pharmaceutical ingredient (paracetamol) and an extruded excipient comprising 75% anhydrous lactose (mainly beta-lactose), 5% anhydrous lactitol and 20% cellulose are compared with tablets having the same load of pharmaceutical ingredient, made with a commercial anhydrous lactose (mainly in beta form). The tableting strength was improved. Further, at higher drug load the commercial product exhibited capping. From this, one may conclude that the inclusion of cellulose is needed to avoid capping. However, it is the inventors finding that the presence of polymeric materials like cellulose are detrimental at high production speed when producing mini-unit dosage forms by a direct compression technique. These materials have a high dwell-time sensitivity. It is contemplated that this is because the presence of such materials increases resiliency of the compressed unit dosage form. Further, cellulose is insoluble in water. The need for a water-insoluble material is undesirable, e.g. if the unit dosage form should be dissolved in water prior to use or should disintegrate in the mouth (this would e.g. be adverse to mouthfeel). In particular, the inventors found in a test wherein mini-tablets were made with an excipient consisting of lactose and lactitol as obtainable by EP 509 606 A1, that the hardness was relatively low.

WO 2006/068484 relates to anhydrous lactose agglomerates comprising at least 50 wt. % beta-lactose crystallites, having a total water content of 0-1.0 wt. %. It is stated to have better compatibility properties compared to regular anhydrous beta-lactose, but also exhibiting good flow properties. The agglomerates are obtained by wet granulation, wherein primary lactose particles are treated with a binder solution. The binder solution can contain one or more saccharides. For preparing tablets of an appreciably higher hardness a binder solution comprising a mixture of lactose, cellulose and sugar alcohols is recommended.

Further, a number of commercially available excipients for making solid dosage forms are known. Dependent on the excipients they may suffer from one or more drawbacks, such as hygroscopicity, high dwell time sensitivity, high lubricant sensitivity, limited in flowability, low bulk density and providing a tablet with a relatively low hardness.

SUMMARY OF THE INVENTION

The inventors now found that a specific lactose-based excipient addresses one or more of the above drawbacks. In particular they found that a specific lactose-based excipient is suitable to make small-sized solid unit-dosage forms, in particular also at a high load of active ingredient and/or at a high production speed.

DETAILED DESCRIPTION OF THE INVENTION

Accordingly, the present invention relates to a method for making a tablet having a diameter, as determined by the longest enveloping circle, in the range of 1 to 5 mm and/or a weight in the range of 1 to 100 mg—comprising an active ingredient selected from the group of pharmaceutical substances and active substances for a dietary supplement or nutraceutical, comprising
 a) providing a lactose agglomerate, preferably comprising anhydrous lactose, more preferably comprising anhydrous beta-lactose, and a sugar alcohol;
 b) providing the active ingredient;
 c) mixing the agglomerate and the active ingredient, thereby obtaining a mixture; and
 d) forming the mixture into the tablet by direct compression.

The invention further relates to a method for preparing a lactose agglomerate, comprising contacting lactose particles, said lactose particles preferably at least substantially consisting of anhydrous lactose, more preferably at least substantially consisting of anhydrous beta-lactose, with an aqueous binding solution comprising a sugar alcohol and optionally a water soluble carbohydrate, preferably lactose, in a fluidized bed, thereby forming agglomerates of the lactose particles, wherein the binding solution is used in an amount of 0.05-0.25 kg per kg dry solids from binding solution per kg lactose agglomerate.

It has surprisingly been found that a lactose agglomerate thus obtained, is suitable to provide a tablet by a direct compression method possessing an appreciably high tensile strength without needing cellulose or another polymer.

The invention further relates to an agglomerate comprising anhydrous lactose, preferably beta-lactose, preferably obtainable by a method for preparing an agglomerate according to the invention, comprising primary anhydrous lactose particles, agglomerated with an agglomerating substance comprising a sugar alcohol, preferably sorbitol, mannitol, maltitol and/or lactitol.

An agglomerate (obtained by a method) according to the invention has been found particularly suitable for use as a filler in the manufacture of the tablet according to the invention. As illustrated by the Examples, it offers amongst others good free-flowing properties and allows the production of, e.g., mini-tablets with excellent mechanical properties, also at a relatively high drug load. It is in particular surprising that this is possible with a single lactose-based filler-excipient, because known commercially available single filler excipients tableting typically provide either good flow or good tablet hardness, but lack of performance on the other condition. Therefore, often mixtures of several excipients are required. Meaning that more effort is required with regard to purchasing, storage, dispensing and maybe blending. The lactose agglomerate (used in a method) according to the invention is a ready-to-go filler excipient providing both, good powder flow and good tabletability, especially in the manufacture of mini-tablets by direct compression. Therefore, less time and money has to be spent on purchasing, storage, dispensing and/or blending than when tablets are prepared from a combination of filler-excipients.

Another advantage is that a direct compression technique can be used instead of e.g. wet granulation, which is a conventional but cumbersome method in the production of tablets requiring several steps for forming the tablets.

The invention further relates to a tablet having a diameter—as determined by the longest enveloping circle—in the range of 1-5 mm and/or a weight in the range of 1-100 mg obtainable by the invention method, the tablet comprising lactose, preferably anhydrous lactose, a sugar alcohol and an active ingredient selected from the group of pharmaceutical substances and active substances for a dietary supplement or nutraceutical.

Unless defined otherwise, all technical and scientific terms used herein have the same meaning as commonly understood by one of ordinary skill in the art. The term "or" as used herein means "and/or" unless specified otherwise.

The term "a" or "an" as used herein means "at least one" unless specified otherwise.

The term "substantial(ly)" or "essential(ly)" is generally used herein to indicate that it has the general character or function of that which is specified. When referring to a quantifiable feature, these terms are in particular used to indicate that it is for at least 75%, more in particular at least 90%, even more in particular at least 95%, even more in particular at least 99% of the maximum that feature.

The term 'essentially free' is generally used herein to indicate that a substance is not present (below the detection limit achievable with analytical technology as available on the effective filing date) or present in such a low amount that it does not significantly affect the property of the product that is essentially free of said substance. In practice, in quantitative terms, a product is usually considered essentially free of a substance, in particular water, if the content of the substance is 0-0.5 wt. %, in particular 0-0.2 wt. %, more in particular 0-0.1 wt. %, based on total weight of the product in which it is present. As will be understood by the skilled person, for certain substances, such as certain aromas or micronutrients, the presence in the starting material may be well below 0.5 wt. %, 0.2 wt. % or 0.1 wt. % and still have a significant effect on a property of the product.

The term "about" in relation to a value generally includes a range around that value as will be understood by the skilled person. In particular, the range is from at least 15% below to at least 15% above the value, more in particular from 10% below to 10% above the value, more specifically from 5% below to 5% above the value.

The term "direct compression" as used herein is generally known in the art and is defined as the process by which tablets are compressed directly from a powder mixture of one or more active pharmaceutical ingredients and suitable excipients. No pretreatment of the powder blend by wet or dry granulation procedure is required.

As used herein, percentages are usually weight percentages unless specified otherwise. Percentages are usually based on total weight, unless specified otherwise.

When referring to a "noun" (e.g. a compound, an additive etc.) in singular, the plural is meant to be included, unless specified otherwise.

For the purpose of clarity and a concise description features are described herein as part of the same or separate embodiments, however, it will be appreciated that the scope of the invention may include embodiments having combinations of all or some of the features described.

The term 'tablet' is generally known in the art. Tablets are characterized by structural rigidity and resistance to changes of shape or volume at 25° C. (and usually well above that temperature, e.g. up to about 100° C. or above). Unlike a liquid, a solid object does not flow to take on the shape of its container, nor does it expand to fill the entire volume available to it like a gas does. The weight of tablets in accordance with the invention generally essentially consists of solid matter which solid matter may be amorphous or crystalline. In principle, the tablets may be porous and contain a gaseous phase. Usually, the tablets are essentially free of a liquid phase.

The size of the tablets in accordance with the invention is relatively small. They are therefore also referred to herein as mini-tablets. In terms of diameter, the diameter, as determined by the longest enveloping circle, of the tablets, in particular the mini-tablets—is usually in the range of 1 to 5 mm, preferably in the range of 1.5 to 4 mm, more preferably in the range of 2.0 to 3 mm. The weight of the mini-tablets is usually in the range of 1-100 mg. Preferably, the weight is at least 3 mg, more preferably at least 5 mg, in particular at least 8 mg, more in particular at 10 mg, even more in particular at least 15 mg. The weight of the mini-tablets is preferably 75 mg or less, more preferably 50 mg or less, even more preferably 40 mg or less, in particular at least 30 mg or less, more in particular 25 mg or less.

The term 'agglomerate' is generally known in the art. Agglomeration by definition is a process during which primary particles are fixed together to form larger, generally porous, secondary particles (the agglomerates). Within these agglomerates individual primary particles are still visible (e.g. by microscopy).

The tablets of the present invention contain an active ingredient, i.e. an ingredient having physiological activity when administered to a subject, in particular a human or other mammal. The active ingredient can be any active ingredient selected from the group of pharmaceutical substances and active substances for a dietary supplement suitable for formulation in tablet. Such ingredients are generally known in the art. Typical examples of active substances for a dietary supplements include vitamins, minerals, fatty acids, amino acids, herbal extracts and antioxidants. In a preferred embodiment, at least one vitamin is present in a tablet of the invention and this vitamin is selected from the group of vitamins A, D, E and K.

The tablet in accordance with the invention is in particular advantageous as a dosage unit for a pharmaceutical substance (also referred to in the art as active pharmaceutical ingredient (API)) of which an effective dose is less than 100 mg per dosage, in particular 0.01-50 mg, more in particular 0.1-25 mg, e.g. 0.2-10 mg. Such pharmaceutical substances are generally known in the art.

In a method for making a tablet according to the invention, a lactose agglomerate is provided comprising lactose and a sugar alcohol. Lactose is the main component of the lactose agglomerate. Typically, the lactose content is at least about 75 wt. % of the agglomerate, preferably 85 wt. % or more, more preferably 90 wt. % or more, in particular 93 wt. % or more. The lactose content of the agglomerate is typically 99 wt. % or less, preferably 98 wt. % or less, in particular 97 wt. % or less, more in particular 96 wt. % or less.

The lactose of the lactose agglomerate can be alpha-lactose, beta-lactose or a combination thereof. Preferably the lactose particles used for preparing the lactose agglomerate at least substantially consist of beta-lactose. Dependent on the preparation method of the agglomerate, also when preparing an agglomerated from beta-lactose primary particles, a part of the lactose of the prepared agglomerate may be alpha-lactose, in particular if alpha-lactose is used as a component of the binding solution for agglomerating primary lactose particles. Usually, the weight to weight ratio alpha-lactose to beta-lactose in the lactose agglomerate is 0:100 to 30:70, preferably 2:98 to 25:75, in particular 5:95 to 25:75, more particular 10:90 to 20:80.

The lactose of the lactose agglomerate can be amorphous or crystalline. In principle the lactose of the lactose agglomerate or a part thereof can be lactose monohydrate. However, as illustrated in the examples, in particular good results have been achieved with a lactose agglomerate, wherein the lactose at least substantially consists of anhydrous lactose. Accordingly, the lactose agglomerate typically comprises 70-99 wt. %, preferably 75-99 wt. %, more preferably 85-98 wt. %, in particular 90-97 wt. %, more in particular 93-96 wt. % anhydrous lactose. The anhydrous beta-lactose content of the agglomerate is usually 70-99 wt. %, preferably 75-99 wt. %, in particular 80-98 wt. %, more in particular 85-98 wt. %.

The lactose monohydrate content of the agglomerate generally is 0-30 wt. %, in particular 0.1-25 wt. %, more in particular 1-10 wt. %, e.g. 2-5 wt. %.

The skilled person knows how to determine the content of anhydrous lactose and lactose monohydrate.

In particular, it is advantageous that at least the primary particles of which the agglomerate is composed at least substantially consist of anhydrous lactose. Preferably, a part of the lactose in the agglomerates acts as a binder (together with the sugar alcohol), the lactose acting as a binder between the primary particles can be lactose monohydrate or anhydrous lactose (which may be formed after drying).

The lactose agglomerate comprises a sugar alcohol. Sugar alcohols are represented by the general formula $HOCH_2(CHOH)_nCH_2OH$. Typically, for a sugar alcohol present in an agglomerate according to the invention, n is an integer in the range of 2-22. Examples of such sugar alcohols are Erythritol (4-carbon), Threitol (4-carbon), Arabitol (5-carbon), Xylitol (5-carbon), Ribitol (5-carbon), Mannitol (6-carbon), Sorbitol (6-carbon), Galactitol (6-carbon), Fucitol (6-carbon), Iditol (6-carbon), Inositol (6-carbon; a cyclic sugar alcohol), Volemitol (7-carbon), Isomalt (12-carbon), Maltitol (12-carbon), Lactitol (12-carbon), Maltotriitol (18-carbon) Maltotetraitol (24-carbon). Polyglycitol is a sugar alcohol with more than 24 carbons.

Preferably, the agglomerate comprises a sugar alcohol having 6 carbons (n=4) or 12 carbons (n=10), more preferably a sugar alcohol selected from the group consisting of lactitol, maltitol, sorbitol and mannitol. Such sugar alcohols, in particular a sugar alcohol selected from the group consisting of lactitol, maltitol, mannitol and sorbitol are, amongst others, particularly suitable to provide solid dosages forms, in particular tablets, with improved tensile strength compared to a sugar alcohol with a lower molecular mass and compared to a commercial lactose agglomerate.

An agglomerate comprising a sugar alcohol with 4, 6 or 12 carbons, such as erythritol, mannitol, lactitol, maltitol or sorbitol are further preferably used in a high-speed tabletting method.

For good binding properties, the sugar alcohol content of the lactose agglomerate generally is at least about 1 wt. %, preferably at least 2 wt. %, more preferably at least 3 wt. %, in particular at least 4 wt. %. Generally the sugar alcohol content of the lactose agglomerate is less than 20 wt. %, preferably less than 15 wt. %, more preferably about 10 wt. % or less, in particular 8 wt. % or less, more in particular 7 wt. % or less, e.g. about 5 wt. % or less.

Usually 50-100 wt. %, preferably 75-100 wt. %, more preferably 90-100 wt. % of the sugar alcohol content is formed by one or more sugar alcohols having 6 or 12 carbons, in particular one or more of the sugar alcohols identified elsewhere herein as preferred, such as one or more sugar alcohols selected from the group of lactitol, maltitol, mannitol and sorbitol.

The contents of lactose and sugar alcohol in the agglomerate usually provide a weight to weight ratio lactose to sugar alcohol of the agglomerate is in the range of 80:20 to 99:1, preferably in the range of 90:10 to 97:3.

The lactose agglomerate usually essentially consists (based on weight) of agglomerates having a size, as determinable by sieving, of 600 µm or less, preferably about 500 µm or less. This has been found advantageous for comp actability properties. Particle size and particle size distribution can suitably be measured using a laser diffraction machine such as a Sympatec Helos F-series using the Rodos dry powder dispersion line and an R5 lens.

Regarding the particle size distribution the $X_{10}$, preferably is in the range of 45-85 µm, more preferably 55-73 µm, in particular about 64 µm.

Regarding the particle size distribution the $X_{50}$, preferably is in the range of 110-220 µm, more preferably 131-200 µm, in particular about 166 µm.

Regarding the particle size distribution the $X_{90}$, preferably is in the range of 230-400 µm, more preferably 268-360 µm, in particular about 314 µm.

$X_{10}$ is the particle diameter corresponding to 10% of the cumulative undersize distribution by volume.

$X_{50}$ (median) means 50% by volume of the particles are smaller than this diameter and 50% are larger.

$X_{90}$ is the particle diameter corresponding to 90% of the cumulative undersize distribution by volume.

For advantageous compactability properties, the lactose agglomerate usually has a poured bulk density (according to USP <616>) in the range of 440-600 kg/m$^3$, preferably in the range of 460-590 kg/m$^3$, in particular 475-575 kg/m$^3$.

The flow function coefficient (FFC, as determinable by Jenicke, see also Examples) of a lactose agglomerate (used in a method) according to the invention is usually at least about 20, preferably at least 25, more preferably 30 or more. In particular, the FFC may be up to 60, more in particular 55 or less, e.g. about 45 or less. Such a high FFC is in particular achievable with a method for preparing an agglomerate according to the invention. As a comparison, commercially available filler excipients typically have a FFC of less than 30. E.g. for Microcelac®100 an FFC of 15 was measured, for Ludipress® an FCC of 19, for SuperTab 24AN an FCC of 25 and for Prosolv SMCC HD 90 an FCC of 15.

Very good results with respect to the manufacture of tablets according to the invention have been achieved with an agglomerate that is essentially free of polymers. It should be noted that polymers, e.g. cellulose-based fillers known in the art have advantages over other known non-polymeric (lactose-based) fillers, but also drawbacks, like increased hygroscopicity or a high dwell-time sensitivity. In accordance with the invention it has been found possible to provide tablets with excellent properties without needing other fillers than the lactose agglomerate. Such essentially polymer-free filler is amongst other advantageous for the preparation of mini-tablets by direct compression, in particular such mini-tables having relatively high active ingredient load, also at a high tabletting speed.

In a preferred, specific embodiment, the lactose agglomerate comprises 75-95 wt. % anhydrous lactose, in particular anhydrous beta-lactose, up to 20 wt. % lactose monohydrate and 1-10 wt. % sugar alcohol, in a wt. to wt. to wt. ratio of about 81 to about 14 to about 5.

In principle the lactose agglomerate can be provided based on a method known in the art, e.g. from WO 2006/068484.

Preferably, the agglomerate is provided by preparing it by spray-agglomerating wherein lactose particles in powder form are agglomerated with an aqueous binding solution comprising the sugar alcohol and optionally a carbohydrate, preferably lactose.

In particular good results have been achieved with a method for preparing a lactose agglomerate, comprising contacting lactose particles (primary particles) at least substantially consisting of lactose, in particular at least substantially consisting of anhydrous lactose, with an aqueous binding solution comprising the sugar alcohol and a water soluble carbohydrate, preferably lactose, in a fluidized bed, thereby forming agglomerates of the lactose particles, wherein the binding solution is used in an amount of 0.05-0.25 kg per kg dry solids from the binding solution per kg lactose agglomerate. Stated alternatively, 0.05-0.25 kg of solids in the binder solution is used per kg of final lactose agglomerate.

Advantageously, for high comp actability of the resultant agglomerate the lactose primary particles have an average size of 60 µm or less, preferably even less than 45 µm. It is preferred to use primary particles having an average size of at least 20 µm, preferably at least 30 µm in order to achieve a compactibility as high as possible. Particle size is as measured with an Alpine Air Jet sieve (Hosakawa Alpine, Germany). For particles below 32 µm, laser diffraction measurement is also suitable (e.g. with a Malvern or a Sympatec).

In particular, an agglomerate with good tabletting properties, and in particular with a high FCC has been found obtainable with a method wherein the binding solution is used in an relatively low amount of dry solids per kg lactose agglomerate, namely to apply the binding solution in an amount of 0.10-0.22 kg per kg dry solids per kg lactose agglomerate, preferably 0.12-0.20 kg per kg dry solids per kg lactose agglomerate, more preferably 0.15-0.20 kg per kg dry solids per kg lactose agglomerate.

In a method for preparing a tablet according to the invention, the provided lactose agglomerate and the provided active ingredient are mixed. This is usually done in a manner known per se, such as by dry-blending. It is further an advantage of the invention that the agglomerate supports active substances well within a wide range of particles sizes of the active substances.

The lactose agglomerate and active ingredient can be blended in a ratio to provide a relatively low active ingredient load, in particular if the active ingredient has a low effective dosage, e.g. a load of less than 20 wt. %, e.g. about 10 wt. % or less. However, the invention has in particular be found advantageous to provide a relatively small unit dosage form, such as a mini-tablet, at a relatively high load of active ingredient. Thus the active ingredient load (the total wt. % of the one or more pharmaceutical substances and active substances for a dietary supplement or nutraceutical, relative to the total weight of the unit dosage form) of a tablet according to the invention is generally at least 20 wt. %, preferably at least 25 wt. %, more preferably 30 wt. % or more, in particular 35 wt. % or more, more in particular at least about 40 wt. %. The maximum load is generally determined by the desired dosage of effective ingredient per dosage unit. Moreover, the chemical-physical properties of the active ingredient plays a role. As the skilled person knows, dependent on the physical-chemical properties of the active ingredient, the active ingredient may adversely affect the flowability of the mixture used to form the tablet. Good free-flowability is in particular important when using a die to form a tablet. The skilled person will know how to address this, based on common general knowledge, the literature cited herein and the information disclosed herein. As illustrated in the Examples, even an active pharmaceutical ingredient like paracetamol, known as a problematic drug to prepare tablets from, can adequately be formulated into a tablet according to the invention at a load of at least about 40%. Usually, the active ingredient is blended with the lactose agglomerate in a ratio to provide an active ingredient load of 80 wt. % or less, preferably 70 wt. % or less, in particular 60 wt. % or less, more in particular 50 wt. % or less. In a specific embodiment, the active ingredient load is about 45 wt. % or less, e.g. about 40 wt. % or less.

If any further excipients are to be used, these may preferably be blended after lactose agglomerate and active ingredient have been mixed. Alternatively they can be blended simultaneously with the agglomerate and/or active ingredient. Such further excipients are optional. If used they can be selected from known excipients for use in the preparation of tablets with lactose excipient as a main excipient component, in particular one or more substances selected from the group consisting of lubricants, disintegrants, flavouring agents, colouring agents. The skilled person will know suitable amounts, based on common general knowledge, the literature cited herein and the information disclosed herein. Usually, the lactose forms 50-99 wt. % of the total excipient content of the (blend used for preparing the) tablet, in particular 75-98 wt. %, more in particular 80-95 wt. %. In general, the total content of excipient components other than lactose and sugar alcohol, and in particular the total content of components other than lactose, sugar alcohol and said active ingredient is 0-15 wt. %, in particular 0.5-6 wt. %, more in particular 1.0-5 wt. %.

Preferably a lubricant, like magnesium stearate is used, preferably in an amount of 0.2-2 wt. %.

Preferably a disintegrant, like crosscarmellose is used, preferably in an amount of 0.2-10 wt. %.

The resultant mixture of active ingredient, lactose agglomerate and optionally one or more other ingredients is then formed into a tablet. The forming step can be based on methodology known in the art per se, e.g. as described in the literature cited herein or references in said literature.

In particular, good results have been achieved with direct compression, which is a generally known technique, wherein a powder mixture is compressed within a die to form a tablet. The various stages typically are as follows: rearrangement, deformation, compaction and relaxation (Jivraj et al, Pharm. Sci. Technolo. Today; Vol 3, No 2 Feb. 2000, pp 58-63).

It is an advantage of the present invention that flowability is good also at high drug load into a die of small dimensions. Moreover, dwell time sensitivity is relatively low, allowing tabletting by direct compression at high speed. High speed is characterized herein in by a dwell time of 60 ms (milliseconds) or less, preferably less than 50 ms, more preferably of 30 ms or less, most preferably 20 ms or less, in particular 10 ms or less. The dwell time is generally more than 0 ms. In practice the dwell time is preferably at least about 1 ms, e.g. about 5 ms or more.

An additional advantage of the invention is that the mini-tablet friability is reduced, compared to mini-tablets made with prior lactose products such as Pharmatose DCL 11 (DMV) as reported in e.g. P. Lennartz et al; "Minitabletting: improving the compactability of paracetamol powder mixtures", International Journal of Pharmaceutics, vol. 173, no. 1-2, 1 Oct. 1998, pp 75-85. Friability is determined according to USP <1216>, and should be lower than 1%.

As indicated above, the invention further relates to a tablet.

In a preferred embodiment, the tablet according to the invention comprises 70-100 wt. % anhydrous beta-lactose, based on total lactose content, more preferably 75-97 wt. % anhydrous beta-lactose, in particular 80-96 wt. % anhydrous beta-lactose, more in particular 90-95 wt. % anhydrous beta-lactose, all based on total lactose content.

In a preferred embodiment, the lactose monohydrate content of the tablet is generally 0-30 wt. %, in particular 0.1-25 wt. %, more in particular 1-20 wt. %, e.g. 2-15 wt. %.

In a particularly preferred embodiment, the tablet has a diameter—as determined by the longest enveloping circle—in the range of 1-5 mm and/or a weight in the range of 1-100 mg, and comprises anhydrous lactose, preferably anhydrous beta-lactose, a sugar alcohol and an active ingredient selected from the group of pharmaceutical substances and active substances for a dietary supplement or nutraceutical, the total of active ingredient(s) forming 20-80 wt. % of the tablet, in particular 30-75 wt. %, more in particular 35-70 wt. %, e.g. 40-60 wt. %. The weight to weight ratio anhydrous lactose to sugar alcohol is preferably 80:20 to 99:1, more preferably in the range of 90:10 to 97:3.

Usually, the tablet according to the invention has a tensile strength, determinable as described in the Examples, of more than 0.7 MPa, preferably of at least 1.0 MPa, more preferably at least 1.5 MPa, in particular at least 2.0 MPa, more in particular at least 2.5 MPa. Typically, the tensile strength is up to about 10 MPa, in particular about 8 MPa or less, more in particular about 7 MPa or less, about 5 MPa or less, e.g. about 3 MPa or less. In a specific embodiment, the tensile strength is about 2 MPa or less.

Example 1: Preparation and Free-Flowing Properties of an Agglomerate According to the Invention Preparation of Spraying Solution:

1.32 kg lactitol monohydrate (Dupont, USA) and 3.68 kg alpha-lactose monohydrate (Pharmatose 200M, DFE Pharma, Germany) were dissolved in 10 kg water. The solution was heated to 70° C. under stirring.

20 kg anhydrous beta-lactose (Lactopress anhydrous fine powder, DFE Pharma, Germany) was fluidized in a spray agglomerator (Aeromatic STREA 70, GEA) operating at an air inlet temperature 80° C. The fluid bed was wetted by atomizing the spraying solution using a two-fluid nozzle at flow rate of 0.5 kg/minute. During the agglomeration process the whole solution was sprayed on the bed.

The product obtained was an agglomerate having a particle size distribution as shown in the following table.

Particle Size Distribution:

| Size fraction (μm) | Typical | 3σ-lower range | 3σ-upper range |
|---|---|---|---|
| $X_{10}$ | 64 | 55 | 73 |
| $X_{50}$ (median) | 166 | 131 | 200 |
| $X_{90}$ | 314 | 268 | 360 |

(determined by Sympatec Helos, using dry dispersion).

Further the agglomerate had the following attributes:

poured bulk density (USP <616>) 530 kg/m³ flow function coefficient according to Jenicke=45, determined as described in: *Properties of powders and bulk solids*, Dietmar Schultze, Ostfalia University for Applied sciences, Wolfenbuttel, Germany, http://www.dietmar-schulze.de/grdle1.pdf.

lactose content 95 wt. %, of which 80% is anhydrous beta-lactose (i.e. 76 wt. % based on total weight of the agglomerate) and 20% (i.e. 19 wt. % based on total weight of the agglomerate) alpha-lactose.

lactitol content 5 wt. %.

moisture content according to Karl Fisher: 1.0 wt %.

Example 2: Comparison of Agglomerate According to the Invention with Roller Dried Lactose Powder A comparative non-agglomerated lactose powder (previously marketed as Pharmatose DCL 40) of anhydrous lactose (95 wt. %) and lactitol (5 wt. %) was made by roller-drying, according to EP 509 606. Compaction performance was compared with the agglomerate obtained in accordance with the invention (as described in Example 1).

Tablets were made from the roller dried lactose powder and from the lactose agglomerate powder of the invention using the following procedure:

All tablet ingredients were conditioned prior to use. The conditioning was done in a lab stove at 20° C. and 30% relative humidity. The lactose powders were carefully weighed and blended in a glass jar using a Turbula mixer. The blending procedure was 15 minutes at 22 rpm. After initial blending, 0.5 wt. % Magnesium Stearate (MgSt) was added and the total mixture was blended again for 5 minutes at 22 rpm.

After mixing, the formulation was tableted by direct compression using a RoTab T rotary lab press. iHolland concave punches with a single tip and die were used.

The rotary tablet press consisted of 5 punches. The rotating frequency was set to 25 Hz and a resulting dwell time of 60 ms. The filling depth of the die was set such that a tablet weight of 250 mg was obtained.

The tablets obtained from the agglomerate in accordance with the invention had increased tensile strength of the tablets at comparable compression pressure, as illustrated by the following table:

Compaction profile for powder of 95 wt. % anhydrous lactose with 5 wt. % lactitol, manufactured using a roller drier (EP509606) respectively Spray agglomerator (Example 1)

| Roller dried powder (EP 509 606) | | Agglomerate of Example 1 according to invention | |
|---|---|---|---|
| Compaction pressure (MPa) | Tensile strength (MPa) | Compaction pressure (MPa) | Tensile strength (MPa) |
| 77 | 0.63 | 78 | 1.28 |
| 156 | 1.83 | 160 | 3.74 |
| 237 | 3.34 | 236 | 6.56 |
| 314 | 4.16 | 311 | 8.45 |

Tensile strength calculation was done according USP<1217>.

Example 3: Comparison of Agglomerate According to the Invention with a Physical Mixture of the Single Ingredients from Example 1

A physical mixture of lactitol and lactose was made as follows: lactitol monohydrate was ground in an oscillating sieve ERWEKA AR400 equipped with a 315 micron sieve. The undersize fraction from the sieve was mixed with spray agglomerated anhydrous lactose (SuperTab 24AN; DFE Pharma) in a ratio of 5 parts by weight Lactitol/95 parts anhydrous lactose in a Turbula mixer at 62 rpm for 8 minutes.

Tablets were made as follows: all tablet ingredients were conditioned prior to use. The conditioning was done in a lab stove at 20° C. and 30% relative humidity. The lactose powders were carefully weighed and blended in a glass jar using a Turbula mixer. The blending procedure was 8 minutes at 62 rpm. After initial blending, 0.5 wt. % Magnesium Stearate (MgSt) was added and the total mixture was blended again for 2 minutes at 62 rpm.

After mixing the formulation was tableted using a RoTab T rotary lab press. iHolland flat beveled punches with a single tip and die were used.

The rotary tablet press consisted of 5 punches. The Rotating frequency was set to 25 Hz and a resulting dwell time of 60 ms. The filling depth of the die was set such that a tablet weight of 250 mg is obtained.

Tensile strength of the resultant tablets was tested, as described in Example 2, and compared with tablets made from the lactose agglomerate, made according to Example 1.

The tablets obtained from the agglomerate in accordance with the invention had increased tensile strength of the tablets at comparable compression pressure, as illustrated by the following table:

Compaction profile of a physical mixture of spray agglomerated anhydrous lactose with 5 wt. % lactitol and co-processed anhydrous lactose with 5% lactitol

| Physical mixture 24AN-5% lactitol | | Agglomerate of example 1 | |
|---|---|---|---|
| Compression pressure (MPa) | Tensile strength (MPa) | Compression pressure (MPa) | Tensile strength (MPa) |
| 81 | 1.09 | 86 | 1.81 |
| 160 | 2.68 | 163 | 4.31 |
| 244 | 4.76 | 238 | 5.78 |
| 302 | 5.91 | 325 | 7.56 |

Example 4: Lactitol Vs Other Binders

Agglomerates were prepared as follows in a Hosokawa Agglomaster AGM-2M PJ-SD. 486 g Anhydrous lactose was used (Lactopress anhydrous fine powder, DFE Pharma, Germany) as starting material. A solution was prepared comprising 30 g of the below specified sugar alcohol and 84 g anhydrous lactose both dissolved in 171 g water. The solution was heated to 60° C. while stirring.

The powder was fluidized and the air inlet temperature of the agglomerator was 115° C. The solution was sprayed at a flow rate of 14 g/min. After the solution was sprayed on the bed completely, the bed was allowed to dry and cool for 20 minutes. The agglomerates were sieved over a 500 μm sieve and the undersize was collected.

The agglomerates are blended with a disintegrant (Primellose, DFE Pharma) according to the mixing procedure described above in example 2 and 3.

Tabletting was done using direct compression on a Kilian single punch (SP-300) tabletting machine. Flat bevelled tooling was used. Tensile strength (TS) at several Compression pressures (CP) were compared with SuperTab 24AN (DFE) in the following Table.

Each of the agglomerates made with a sugar alcohol outperformed the comparative example.

Lactitol Vs Other Binders

| SuperTab 24AN | | Agglomerated with lactitol | | Agglomerated with Maltitol | | Agglomerated with Sorbitol | |
|---|---|---|---|---|---|---|---|
| CP (MPa) | TS (MPa) | CP (MPa) | TS (MPa) | CP (MPa) | TS (MPa) | CP (MPa) | TS (MPa) |
| 81 | 0.98 | 81 | 1.66 | 81 | 2.04 | 81 | n.a. |
| 162 | 2.76 | 162 | 3.45 | 162 | 4.90 | 162 | 5.66 |
| 242 | 4.44 | 242 | 5.77 | 242 | 6.44 | 242 | 6.45 |
| 324 | 5.55 | 324 | 6.83 | 324 | 7.23 | 324 | 6.76 |

Example 5: Drug Load Testing

The agglomerate of Example 1 was mixed with a model drug, paracetamol, an often used model drug because it is known to be a drug difficult to use in formulations at a high load. A fine grade of paracetamol was chosen ($x_{50}$=38 μm). To this formulation 4% cross carmellose sodium was added and blended in a Turbula mixer for 8 minutes at 62 rpm.

After initial blending 1% MgSt was added and again blended for 2 additional minutes. The formulation was tableted using direct compression on a rotary lab tablet press, RoTab T using iHolland concave punch multi tips and dies (*7), rotating frequency 25 Hz, the resulting dwell time was 60 msec. Filling depth of the die was set such that tablets of a weight of 20 mg were obtained.

This procedure was repeated for the preparation of a comparative tablet, using two commercially available excipients, known for their good free-flowing properties, namely agglomerated Micro Crystalline Cellulose (Pharmacel MCC102, DFE Pharma) and agglomerated anhydrous lactose (SuperTab 24AN).

Results are shown in the following table.

Drug loading of tablets with a diameter of 3 mm according to the invention compared with tablets having the same dimensions made from a standard high performance formulation of 50% spray agglomerated anhydrous lactose with 50% MCC102:

| % Paracetamol | 50% spray agglomerated anhydrous lactose + 50% MCC102 Tensile strength (MPa) | Agglomerate of Example 1 Tensile strength (MPa) |
|---|---|---|
| 0 | 2.4 | 3.1 |
| 5 | 2.6 | 3.8 |
| 12.5 | 2.1 | 3.4 |
| 20 | 1.7 | 2.2 |
| 25 | 1.7 | 1.8 |
| 30 | 2.0 | 1.7 |
| 35 | No flow | 1.4 |
| 40 | No flow | 1.0 |

It was found that satisfactory tensile strength was reached, also at a high load. Flowing problems were observed for the comparative excipient at a load of 35% paracetamol and higher, whilst mini-tablets made from a blend of 40% paracetamol and 60% lactose agglomerate according to Example 1 still had satisfactory flowing properties to produce mini-tablets of satisfactory quality, including sufficient tensile strength.

Example 6: Tablet Tensile Strength (TTS) and Friability of Minitablets

A comparative test was carried out to compare Pharmatose DCL 11 (DMV) and the agglomerate of the invention as prepared in example 1.

Pharmatose DCL 11 is presently marketed as Supertab 11 SD, available from DFE Pharma, GmbH, Germany. These products are identical.

Minitablets of 20 mg and 3 mm having varying drug (paracetamol) loads were prepared as follows:

| Name of Ingredient | Product | Name of Source |
|---|---|---|
| Agglomerate from example 1 | Agglomerated anhydrous lactose and lactitol (excipient) | DFE Pharma |
| SuperTab ® 11SD | Spray dried lactose (excipient) | DFE Pharma |
| Primellose ® | Croscarmellose sodium | DFE Pharma |
| Magnesium stearate | Magnesium stearate | Sigma-Aldrich |

Micronized paracetamol was obtained from Acros Organics (force sieved 315 micron. Particle size distribution (laser diffraction):

| | x10 (μm) | x50 (μm) | x90 (μm) |
|---|---|---|---|
| Acros Organics (force sieved 315 micron) | 10 | 38 | 203 |

Climatizing of Powder

All powders used (with exception of magnesium stearate) are prior to blending stored overnight in a Heraeus climate chamber. Temperature is 20° C. and relative humidity (RH) is 30%.

Blending and Sieving 0-40 wt. % Micronized paracetamol is added to the formulation containing either SuperTab 11SD (DCL 11) or the agglomerate of example 1, and both tests further contained 4 wt. % Primellose and 1% magnesium stearate. Prior to the addition of the excipient formulation mixture the paracetamol is sieved over a 315 μm sieve using a Erweka AR400 oscillating sieve to remove agglomerates. A Sandwich procedure is applied for the addition of paracetamol: about 50% of the excipient mixture is pre-filled in a jar, then desired amount of paracetamol is added and the mixture is filled with the remaining 50% of excipient mixture. In a last step the Primellose is added. The jar is placed in the Turbula T2F blender for 8 min at 62 rpm and in a second mixing step Magnesium Stearate is mixed for 2 minutes at 62 rpm.

Tabletting

Tablets were compressed using a Luxner RoTab T rotary press, rotating frequency:

25 rpm, with a resulting dwell time of 60 ms
50 rpm, with a resulting dwell time of 30 ms.

Filling depth of the die is set such that tablets of a weight of 20 mg (for mini tablets) are obtained.

For mini tablets iHolland 3 mm concave punch multi tips and dies (*7) are used. Tablets were produced using a compaction force of 12 kN for series A) (60 ms), and 7 kN (for series B, 30 ms). Pharmaceutical industry prefers to apply limited force to the punches as mini tablet punches are very fragile. The pressure of 12 kN is high for the industry and ideally high tablet tensile strength (TTS) is achieved with low compaction force.

Conditions on the lab during all tabletting experiments were t=20-23° C. and RH 39-44%.

Tablet Weight and Hardness Testing

Mini tablets were analysed on the Sotax SmartTest 50 with proven Dr. Schleuniger® Pharmatron measuring technology. Hardness is tested using a constant speed of 0.35 mm/s.

Compaction (Tabletting) is usually portrayed as a compaction profile, tablet tensile strength (TTS) (derived from tablet crushing strength (TCS)) against compaction force or pressure (force per unit area) as this value is independent of tablet size.

For concave tablets, the tablet tensile strength can only be calculated with an additional value for the cylinder height (W) or the cupheight (hc):

$$TTS = \frac{10 \cdot TCS}{\pi \cdot D^2 \cdot \left[\frac{2.84 \cdot H}{D} - \frac{0.126 \cdot H}{W} + \frac{3.15 \cdot W}{D} + 0.01\right]} =$$

-continued $$\frac{10 \cdot TCS}{\pi \cdot D^2 \left[\frac{2.84 \cdot H}{D} - \frac{0.126 \cdot H}{H - 2 \cdot h_c} + \frac{3.15 \cdot (H - 2 \cdot h_c)}{D} + 0.01\right]}$$

(K. Pitt, M. Heasley, 2013, Powder technology edition 238, Determination of the tensile strength of elongated tablets)

He for the concave tooling 3 mm is 0.25 mm

Friability

2 Grams of 20 mg minitablets was used to test friability. Tablets are carefully dedusted on a tissue and weighed prior to testing. Tablets are placed in a drum and rotated for 100 times (25 rpm, 4 min). Tablets are removed, dedusted and accurately weighed. A maximum mean weight loss from the three samples of not more than 1.0% is considered acceptable for most products according to USP <1216>.

Results

In the following table, the results of the tablet tensile strength and friability measurements are shown:

Series A): Tablet tensile strength (TTS) and Friability results of mini tablets 3 mm 20 milligram produced at 12 kN 25 rpm with Rotary press containing SuperTab 11SD and Agglomerate according to the invention and drug loading of 0, 20 and 40 wt. % paracetamol

|  | 0 wt. % paracetamol | | 20 wt. % paracetamol | | 40 wt. % paracetamol | |
| --- | --- | --- | --- | --- | --- | --- |
|  | TTS (MPa) | Friability (%) | TTS (MPa) | Friability (%) | TTS (MPa) | Friability (%) |
| SuperTab 11SD | 1.82 | 0.26 | 0.95 | 0.63 | 0.71 | 2.07 |
| Agglomerate according to the invention (ex. 1) | 5.69 | 0.22 | 3.19 | 0.52 | 1.49 | 0.72 |

Series B): Tablet tensile strength (TTS) of mini tablets 3 mm 20 milligram produced at 7 kN 50 rpm with Rotary press containing SuperTab 11SD and Agglomerate according to the invention and drug loading of 40 wt. % paracetamol

|  | TTS (MPa) |
| --- | --- |
| Supertab 11 SD (DCL 11) | 0.35 |
| Agglomerate according to the invention | 1.0 |

From the above tables it is clear that minitablets made with the product according to the invention have a much higher tensile strength as compared to minitablets produced with Pharmatose DCL 11 (=Supertab 11 SD); in addition, by using the agglomerate of the invention, the resistance of minitablets against attrition is significantly improved, especially at high drug loads; the friability stays well below 1%, whereas the minitablets prepared with DCL 11 have a friability of even more than 2%, which is unacceptable for minitablets.

The invention claimed is:

1. A method for making a tablet having a diameter, as determined by the longest enveloping circle, in the range of 1 to 5 mm and/or a weight in the range of 1 to 100 mg, the method comprising:
(a) agglomerating in a fluidized bed anhydrous lactose particles with an aqueous binding solution comprising
(i) a sugar alcohol selected from the group consisting of lactitol, maltitol, sorbitol, mannitol and erythritol, and
(ii) a water soluble carbohydrate comprising alpha-lactose monohydrate, thereby forming agglomerates of the lactose particles, wherein the binding solution is used in an amount of 0.05-0.25 kg dry solids in the binding solution per kg lactose agglomerate, and wherein the agglomerates comprise 80-99 wt. % anhydrous lactose and have a size, as determinable by sieving, of 600 μm or less;

(b) mixing the agglomerates with an active ingredient, and optionally one or more excipients, thereby obtaining a mixture; and (d) forming the mixture into the tablet by direct compression.

2. The method according to claim 1, wherein the tablet comprises at least 20 wt. %, based on total weight of the tablet, the active ingredient.

3. The method according to claim 2, wherein the tablet comprises 30-80 wt. %, based on total weight of the tablet, the active ingredient.

4. The method according to claim 1, wherein agglomerating is spray-agglomerating.

5. The method according to claim 1, wherein the weight to weight ratio of total lactose to sugar alcohol in the agglomerate is in the range of 80:20 to 99:1.

6. The method according to claim 5, wherein the weight to weight ratio of total lactose to sugar alcohol in the agglomerate is in the range of 90:10 to 97:3.

7. The method according to claim 1, wherein the agglomerate comprises 90-99 wt. % anhydrous lactose.

8. The method according to claim 7, wherein the agglomerate comprises 90-95 wt. % anhydrous lactose.

9. The method according to claim 1, wherein the compression is carried out at a dwell time of 60 ms or less.

10. A method for preparing a lactose agglomerate filler in the manufacture of tablets, comprising:

agglomerating in a fluidized bed anhydrous lactose particles with an aqueous binding solution comprising (i) a sugar alcohol selected from the group consisting of lactitol, maltitol, sorbitol, mannitol and erythritol, and (ii) a water soluble carbohydrate comprising alpha-lactose monohydrate, thereby forming agglomerates of the lactose particles, wherein the binding solution is used in an amount of 0.05-0.25 kg dry solids in the binding solution per kg lactose agglomerate, wherein the agglomerates comprise 80-99 wt. % anhydrous lactose and have a size, as determinable by sieving, of 600 μm or less.

11. The method according to claim 10, wherein the anhydrous lactose is anhydrous beta-lactose.

12. The method according to claim 10, wherein the binding solution is used in an amount of 0.15-0.20 kg dry solids per kg lactose agglomerate.

13. The method according to claim 10, wherein the agglomerating is spray-agglomerating.

14. The method according to claim 10, wherein the weight to weight ratio of total lactose to sugar alcohol in the agglomerate is in the range of 80:20 to 99:1.

15. The method according to claim 14, wherein the weight to weight ratio of total lactose to sugar alcohol in the agglomerate is in the range of 90:10 to 97:3.

16. The method according to claim 10, wherein the agglomerate comprises 90-99 wt. % anhydrous lactose.

17. The method according to claim 10, further comprising mixing the agglomerates with an active ingredient, excipient, or both.

18. The method according to claim 10, wherein the agglomerates do not comprise cellulose.

19. The method according to claim 10, wherein the agglomerates do not comprise polymers.

* * * * *